United States Patent [19]

Pangburn

[11] Patent Number: 4,712,552

[45] Date of Patent: * Dec. 15, 1987

[54] CUSHIONED ABRASIVE COMPOSITE

[75] Inventor: William E. Pangburn, Ventura, Calif.

[73] Assignee: William W. Haefliger, Pasadena, Calif. ; a part interest

[*] Notice: The portion of the term of this patent subsequent to Jul. 17, 2001 has been disclaimed.

[21] Appl. No.: 831,808

[22] Filed: Jun. 23, 1986

Related U.S. Application Data

[63] Continuation of Ser. No. 580,190, Feb. 15, 1984, abandoned, which is a continuation-in-part of Ser. No. 356,830, Mar. 10, 1982, Pat. No. 4,459,987.

[51] Int. Cl.$^4$ .......................... A61B 17/00; B24B 3/46
[52] U.S. Cl. ....................................... 128/355; 51/401; 132/76.4
[58] Field of Search .......... 128/355; 51/391, 394–409; 132/76.4

[56] References Cited

U.S. PATENT DOCUMENTS

| | | | |
|---|---|---|---|
| 3,129,540 | 4/1964 | Valles | 51/391 |
| 3,653,859 | 4/1972 | Zimmer, Jr. et al. | 51/401 |
| 3,785,094 | 1/1974 | Holzhaver | 51/401 |
| 3,862,522 | 1/1975 | Mednick | 51/400 |
| 4,459,987 | 7/1984 | Pangburn | 128/355 |

Primary Examiner—Andrew H. Metz
Assistant Examiner—Chung K. Pak
Attorney, Agent, or Firm—William W. Haefliger

[57] ABSTRACT

An abrasive and cushioned composite comprising:
(a) a tough, stretchable first sheet of silicone polymer,
(b) abrasive particulate adherent to and protruding from at least one side of the first sheet,
(c) other sheet means providing a cushioned support for said first sheet and combined therewith.

10 Claims, 19 Drawing Figures

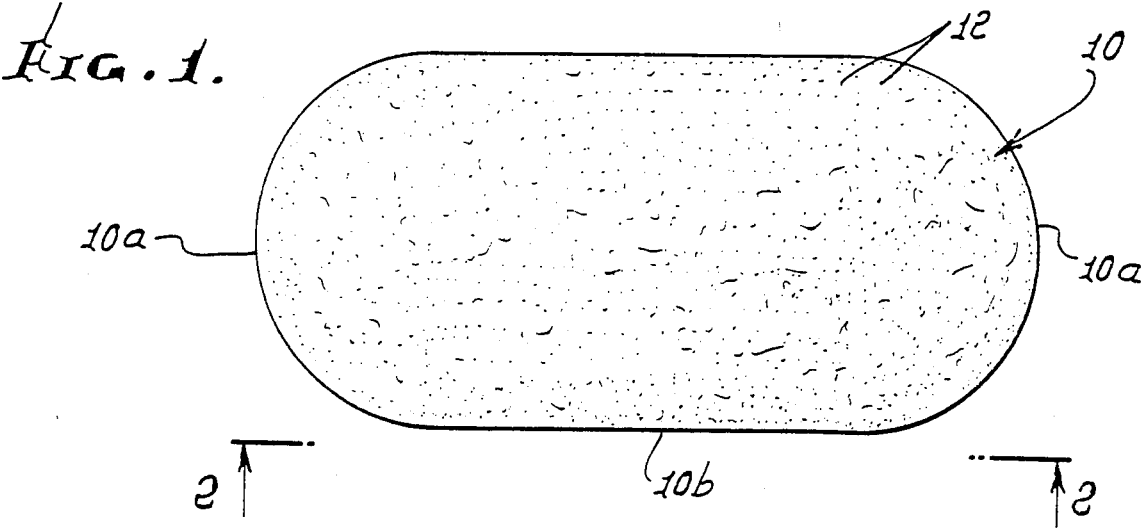
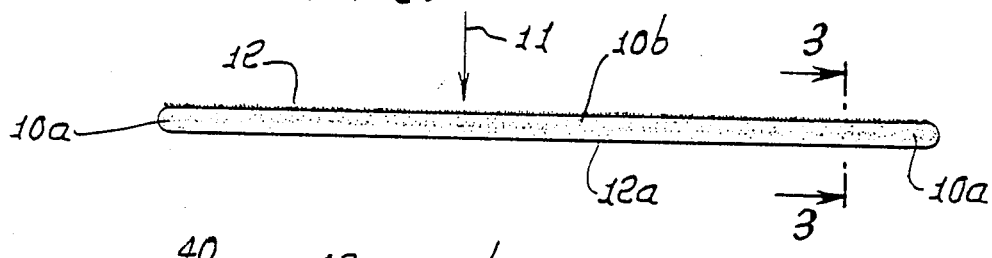
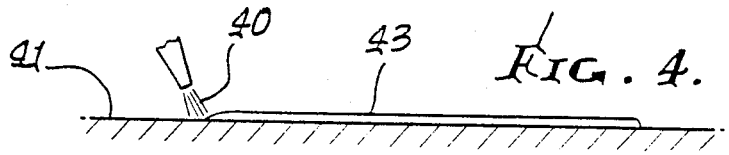
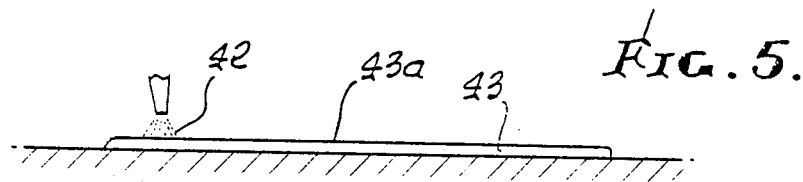
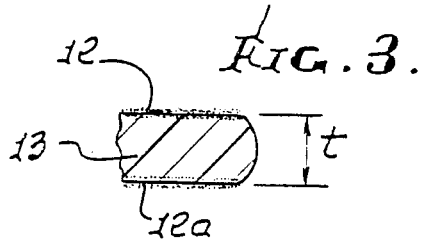
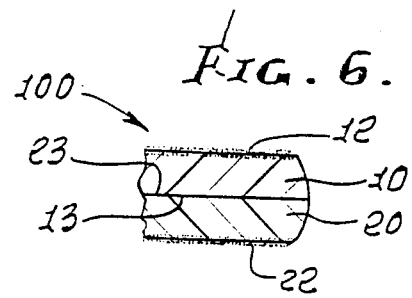
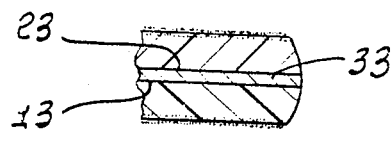
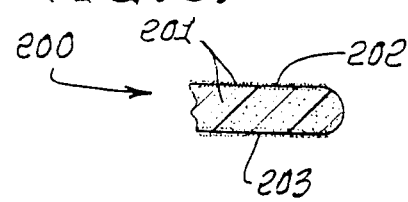

CUSHIONED ABRASIVE COMPOSITE

BACKGROUND OF THE INVENTION

This is a continuation of application Ser. No. 580,190 filed Feb. 15, 1986, now abandoned, which is a continuation-in-part of my prior application Ser. No. 356,830 filed Mar. 10, 1982, now U.S. Pat. No. 4,459,987.

This invention relates generally to abrasive devices, and more particularly concerns a tough, flexible and stretchable abrasive sheet that may be die cut or formed to many configurations useful in abrading skin or finger (or toe) nail surfaces as during callous removal, dermabrasive and other skin removal techniques, as well as other work surfaces, and which is cushioned by other sheet means.

At the present time, rigid abrading stones and unstretchable devices are manipulated to effect skin removal. Such rigid or unstretchable devices do not desirably conform to complexly curved skin contours, as for example at heels, elbows, etc. and consequently they are difficult to manipulate accurately to remove skin at selected areas only. As a result, skin "burns" can and do occur, and excess time is consumed in achieving selected skin area removal. There is need for a means which will obviate these difficulties, and which provides cushioning to facilitate controlled abrasive removal of skin, nail, and other work surfaces.

SUMMARY OF THE INVENTION

It is a major object of the invention to provide a stretchable, variable shape material offering a solution to the above difficulties. Basically, the stretchable cosmetic abrasive sheet of the invention comprises a tough, shaped, flexible sheet of silicone rubber and abrasive particulate, compounded so that at least one side of the sheet will have particulate exposed edges for rubbing contact with human skin during use. As will be seen this sheet is preferably stretchable and compressible to enhance its compatability to skin contours such as heels and elbows; further, the particulate preferably comprises pumice particles or the like. Also, the sheet thickness is between 0.015 and 0.100 inches. Further, two such sheets may be bonded together to provide a composite sheet, as will be seen.

The method of making the described sheet comprises the steps;

(a) forming a layer of incompletely cured silicone rubber, (b) combining abrasive particulate such as pumice with the rubber to adhere thereto, and (c) allowing the layer to cure to form a sheet with the particulate exposed at one side thereof for ultimate rubbing contact with human skin during use.

As will appear, the silicone-pumice initially contains a curing agent which disperses as the sheet cures.

An additional object is to provide other sheet means supporting a stretchable polymerized resin sheet carrying abrasive, the other sheet means providing cushioned support and combined with the first sheet and its carried abrasive.

These and other objects and advantages of the invention as well as the details of an illustrative embodiment, will be more fully understod from the following description and drawings, in which:

BRIEF DESCRIPTION OF THE DRAWINGS

FIG. 1 is a plan view of a die cut or formed sheet or pad embodying the invention;

FIG. 2 is an edge view taken on lines 2—2 of FIG. 1;

FIG. 3 is an enlarged fragmentary section taken on lines 3—3 of FIG. 2;

FIG. 4 is an elevation showing one step in formation of the FIG. 1 sheet or pad;

FIG. 5 is a view like FIG. 4 showing another step in formation of the sheet or pad; and FIGS. 6, 7 and 8 are views like FIG. 3 showing modified sheet or pad constructions;

DETAILED DESCRIPTION

Figure 9:
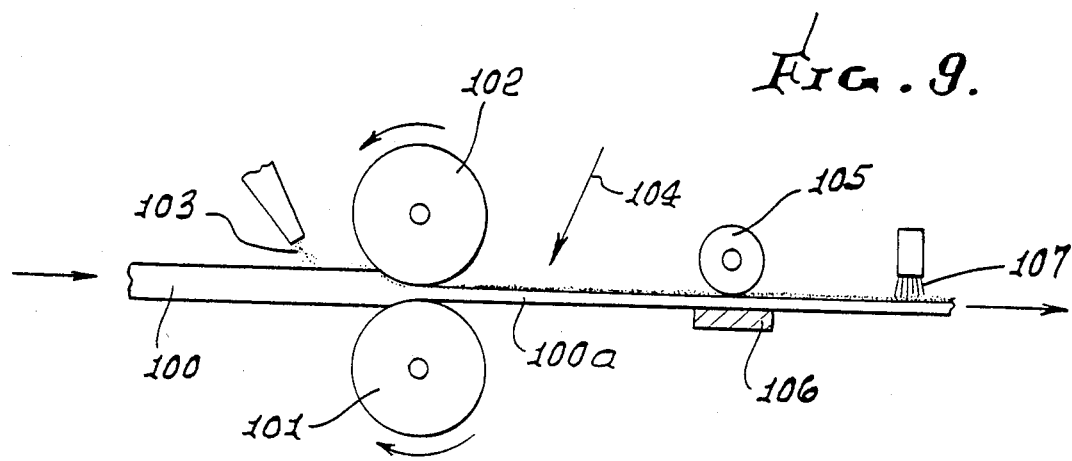
FIG. 9 is a side view showing a modified method of forming the silicon layer.

In FIGS. 1-3, a flexible, flat abrasive sheet is shown at 10, it also being somewhat stretchable to conform to contours of the body such as heels, elbows, etc. The sheet is also resiliently compressible in the direction 11, normal to the plane it defines. The sheet may preferably be die cut to shape, as for example lengthwise elongated, with rounded ends as at 10a.

The sheet preferably consists of pourable silicone polymer or adhesive sealant as for example General Electric RTV 108 which vulcanizes at room temperature. It contains a suitable curing agent. Also usable is GE RTV 118 which is self leveling when poured on a surface. RTV 108 and 118 are both translucent, tough and durable. The sheet is loaded with, or carries, abrasive particulate such as pumice or other fine abrasive suitable to abrading thickened areas of the skin. As shown, the protruding particulate 12 is located at at least one side of the sheet, and exposed for rubbing contact with the skin. FIG. 3 shows another like layer 12a at the opposite side of the sheet. The central layer 13 of silicone carries the particulate layers which are bonded to the silicone during curing, edges of particles penetrating the silicone mass. Note that particulate also covers the sheet or pad peripheral edges, as at 10b and 10a in FIG. 2, but this may be omitted.

Typically, the sheet thickness "t" is between 0.015 and 0.100 inches, and preferably between 0.020 and 0.060 inches.

In FIG. 6, the sheet or pad 100 includes a first sheet 10 having particulate 12 on one side, and a second sheet 20 having particulate 22 on one side. The two sheets have their opposite sides 13 and 23 bonded together as during curing so that the particulate layers 12 and 22 are exposed at opposite sides of the pad. In FIG. 7 the construction is the same, excepting for a separate bonding layer 33 attached to sides 13 and 23. Layer 33 may consist of polyester matte or other stretchable flexible fiber. FIG. 8 shows a modified sheet or pad 200 impregnated with particulate 201. so that edges of the particulate are exposed at the opposite sides of the sheet, 202 and 203 indicating such edges.

The method of making the pad is shown in FIGS. 4 and 5. In FIG. 4 the silicone polymer, is poured or spread at 40 on a flat surface 41. That surface advantageously consists of polyethylene at room temperature, so that the silicone will not adhere to same. Pumice particles are than dispensed as at 42 to cover the upper side 43a of the silicone layer 43 prior to complete curing. The particles become bonded to the silicone, and as the latter cures, the acetoxy or other curing agent vaporizes. The resultant sheet or pad has generally uniform thickness, and may be cut to shape. After about 15 to 20 minutes from time of pour at 40, the silicone layer or sheet is cured, at room temperature.

One usable silicone formulation is known as dimethyl polysiloxane, and the curing agent is acetic anhydride.

Another feature of the invention is to embody a finer grade of particle fineness at layer 12, and a coarser grade of particle fineness at layer 12a, as in FIG. 3.

Representative finenesses are as follows:

Fineness "A" (passes Tyler screen of mesh size 60, but will not pass screen mesh 80).

Fineness "B" (passes Tyler screen of mesh size 120, but will not pass screen mesh 140).

In FIG. 9, the sheet 100 (corresponding to sheet 10), prior to complete curing, is reduced in thickness, as by passage between calender rolls 101 and 102, thereby to form the final sheet 100a. Pumice such as particulate may be dispensed at 103 onto the upper surface of the sheet prior to passage of the sheet between the rolls, in which event the pumice is pressed into the sheet as by the roll 102. Alternatively, the pumice may be dispensed at 104 onto the sheet after it emerges from between the rolls 101 and 102. A presser unit, such as roller 105, may then be used to press the pumice into the sheet 100a as it slides over a backer 106, prior to completion of cure. A brush or compressed air stream, at 107, removes excess pumice from the sheet.

Figure 10:
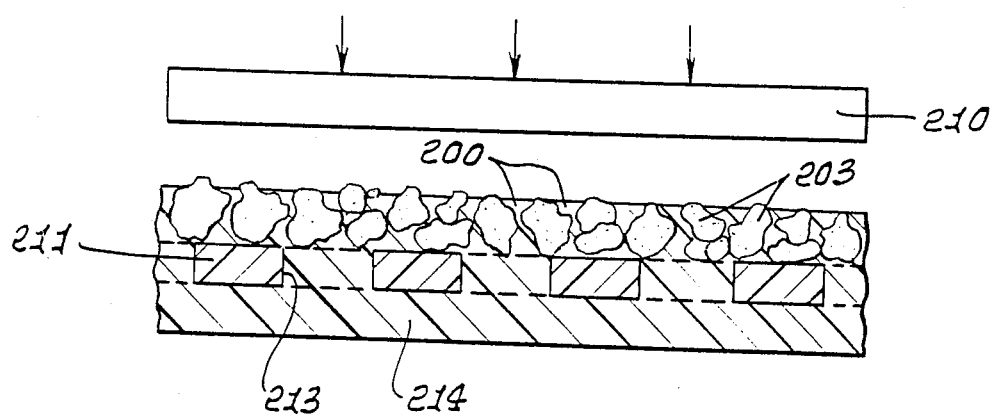
FIG. 10 is an enlarged side elevation showing a method of pressing particulate into the silicone layer.
Figure 10A:
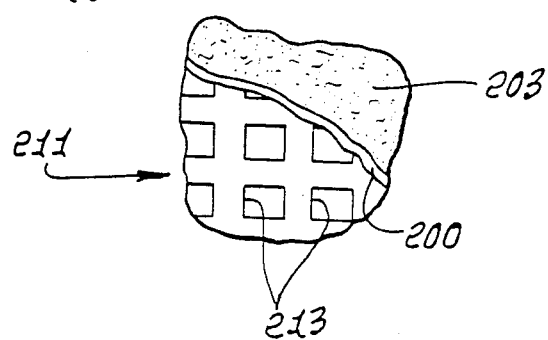
FIGS. 10a shows a matte on which the silicone layer may be formed.

In FIGS. 10 and 10a the pumice particles 203 are shown as having been pressed, as by bar 210, into the silicone layer 200, so that the particle edges protrude from the layer 200. A matte sheet 211 in layer or sheet 200 supports the pumice, as shown. The matte contains mesh openings 213 into which the silicone layer extends, i.e. matte 211 is embedded in layer 200 and offers additional support to same. The matte may consist of polyester, Nylon, etc; it is stretchable (to stretch with layer 200); and it typically has a loose weave or configuration.

If desired, the FIG. 10 sheet can be inverted, and pumice particles pressed into area 214, in the same manner as particles 203 extend in layer 200.

Figure 11:
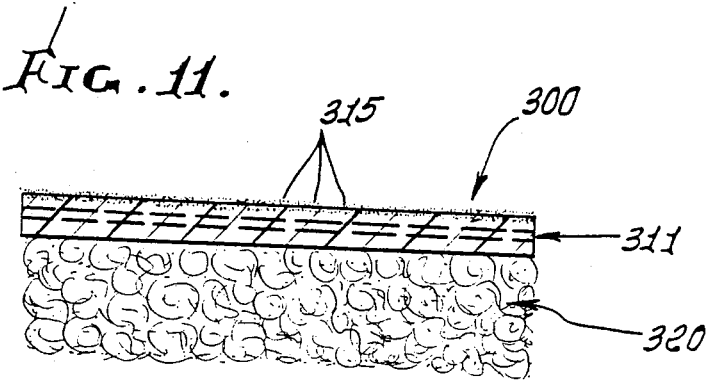
FIGS. 11-14 are elevations showing modifications.

In FIG. 11, the flexible first sheet is like that shown at 200 in FIG. 10, with a matte 311 embedded in the silicone polymer layer 300. Particulate (pumice for example) particles 315 are carried by the layer 300, as in FIG. 10, with edges exposed at a first side for relatively heavy duty dermabrasion (elbows, feet, etc.). A second sheet or layer 320 of reticulated foam that is resiliently compressible is attached to the sheet or layer 300, and projects at the second side thereof, as shown. The attachment may be effected by contacting one side of layer 320 with the uncured or partially cured layer 300, and allowing the cure to proceed to completion. Examples of the open work, fibrous sheet 320 are:

No. 3 Scott Industrial Foam, a reticulated polyester urethane product of Wilshire Foam Products Inc. Carson, California No. 4 Scott Safety Foam, reticulated urethane ester product of Wilshire Foam Products, Inc.

Such foam is useful for lighter dermabrasion and cleaning as well as massaging of more sensative skin areas, as face and neck. Thus, one device, as in FIG. 11, may have multiple functions, and the functional layers assist in supporting one another. Also, the openwork layer 320 is easily cleaned or freed of removed skin particles and soils, as by washing.

Figure 12:
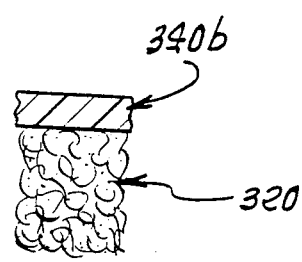
Figure 13:
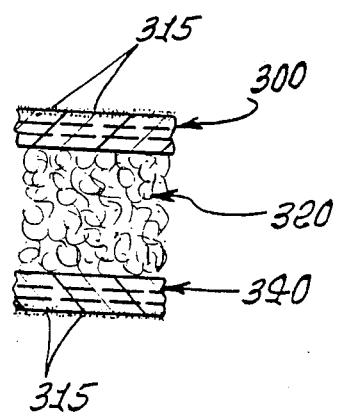
Figure 14:
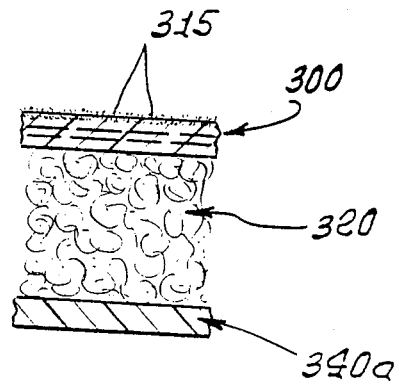

The device of FIG. 13 is like that of FIG. 12, and a third layer 340 is attached to the opposite side of the second layer 320. Third layer 340 is like layer 300, whereby the dermabrasion layers are interconnected by compressible layer 320. FIG. 14 is like FIG. 13, excepting that layer 340a contains no particulate. FIG. 12 is like FIG. 14, excepting that no layer 300 is used, layer 340b contains no particulate, and may consist of flexible, tough material.

Layer 320 is characterized as remaining distended after use; it does not "yellow" or discolor; and it has excellent wet abrading capability.

The thicknesses of layers 300, 340 and 340a are exaggerated in FIGS. 11–14.

Figure 15:
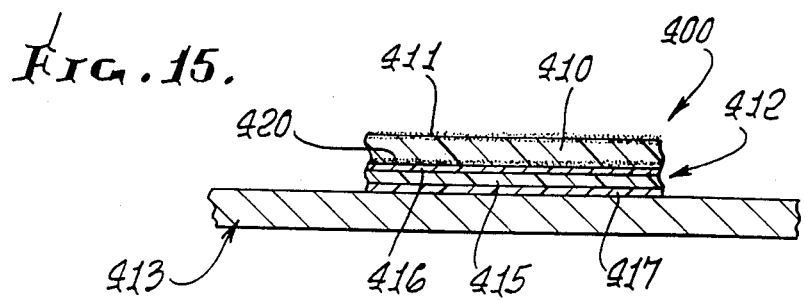
FIG. 15 is a section through a composite sheet assembly showing a cushioned support for the abrasive sheet.

In FIG. 15 the composite 400 includes a tough, stretchable and flexible first sheet 410 of polymer resin, silicone polymer being of unusual advantage. It has abrasive particulate 411 adherent to and protruding from one side, whereby the particulate (examples being pumice as described above, or, silicon carbide or aluminum oxide) is exposed for abrasive use. Other sheet means 412 is combined with the first sheet 410 to provide cushioned support therefor, as for example when the composite is mounted on a manipulatable carrier 413. One example of the latter is an elongated fingernail file which is manually maniupulatable.

The thickness of sheet 410 is typically between 0.015 inch and 0.150 inches, and preferably is uniform and between 0.020 and 0.060 inches.

Figure 17:
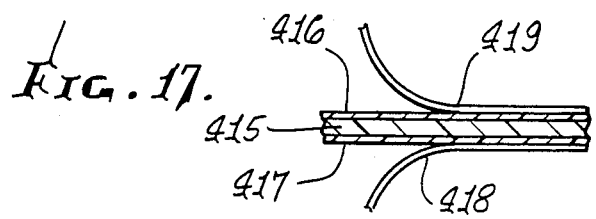
FIG. 17 is a section through a cushioned support, showing removal of adhesive protection film.

The other sheet means 412 is shown to comprise a second sheet 415 of polymerized resin, an example being a polyester sheet about 0.001 inch in thickness. It has adhesive layers 416 and 417 at and on its opposite sides, whereby layer 416 adheres firmly to the first sheet, and the second layer 417 may be exposed (as by removal or peel-off of a protective strip 418 as shown in FIG. 17) for attachment to carrier 413. Likewise, a protective strip 420 may be initially peeled away from adhesive layer 416 to permit its adherence to sheet 410, as via particulate 420 on the side of sheet 410 facing the adhesive 416. Such particulate may consist of abrasive particulate (pumice for example) as described above, in FIGS. 3 and 8.

The FIG. 17 second sheet 415, adhesive layers 416 and 417, and protective strips 418 and 420 is known, and is produced as for example by Minnesota Mining and Manufacturing (MMM).

Figure 16:
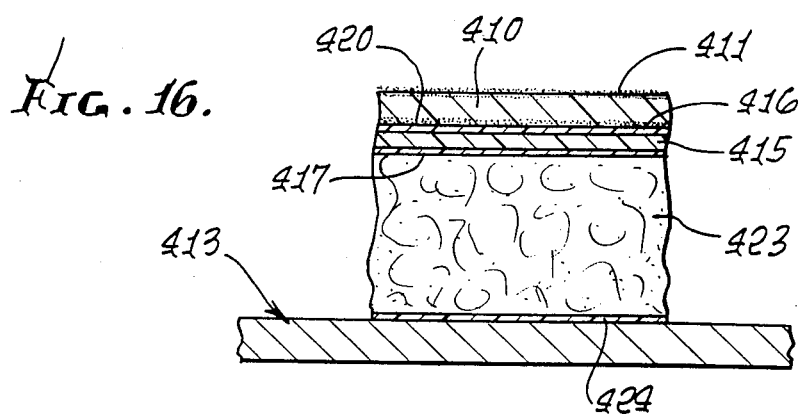
FIG. 16 is like FIG. 15, and showing additional cusioned support for the abrasive sheet.

FIG. 16 composite repeats what is shown in FIG. 15, and to that extent the elements bear the same identifying numerals. In addition, a third and relatively much thicker sheet 423 is provided, that consists of compressible foam (examples being polyurethane, polyethylene and polyvinyl chloride). One side of sheet 423 may be compressively bonded to the second sheet, as via adhesive layer 417, and its opposite side may be adhesively bonded by an adhesive layer 424 to a carrier 413, as referred to in FIG. 15. Accordingly, additional or much greater cushioning is provided for the exposed abrasive layer 411, i.e. a "super cushion". Sheet 423 is typically between ¼ and 1/16 inch in thickness.

Such cushioning is found to be desirable for control of abrasion of work surfaces, as for example locally curved surfaces, the abrasive then conforming more closely to the work curvature during its back and forth application to such surfaces. Without such cushioning, the abrasive will tend to abrade too much in certain areas, and not enough in others.

Figure 18:
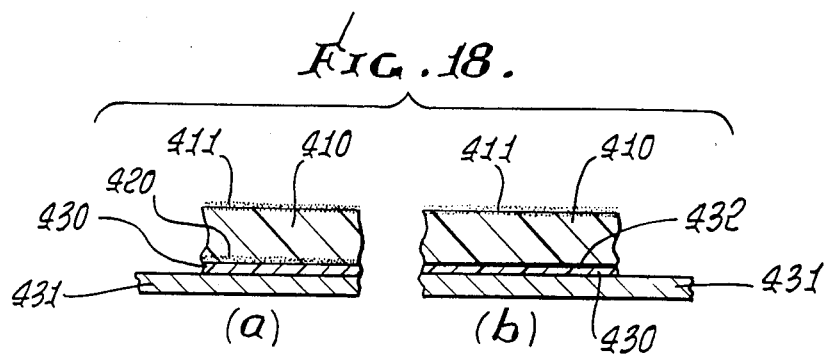
FIGS. 18 and 19 are modified composites.

In the FIG. 18a composite, the numerals 410, 411 and 420 identify the same elements as in FIG. 15. In addition, other sheet means providing a support for the first sheet 410 and combined therewith includes a thin release liner 430 bonded to the particulate layer 420, and a paper layer or sheet 431 attached to the opposite side of the release liner, and carrying same. In FIG. 18(b) the composite is the same, except that particulate 420 is omitted, and the release liner 430 is firmly bonded to the side of first sheet 410, at 432. The release liner is a hardened, thin, polydimethyl siloxane coating on the paper layer, which penetrates and locks to the fibers of the paper as it shrinks during cooling (the coating is applied using a tin curing solvent system, at elevated temperature). One example is GP Dow #23 paper coating sold under the name "Syloff." The thickness of the release liner is between about 0.001 and 0.005 inches. Another commercial example is General Electric SS 4191, known as a silicone primer.

Figure 19:
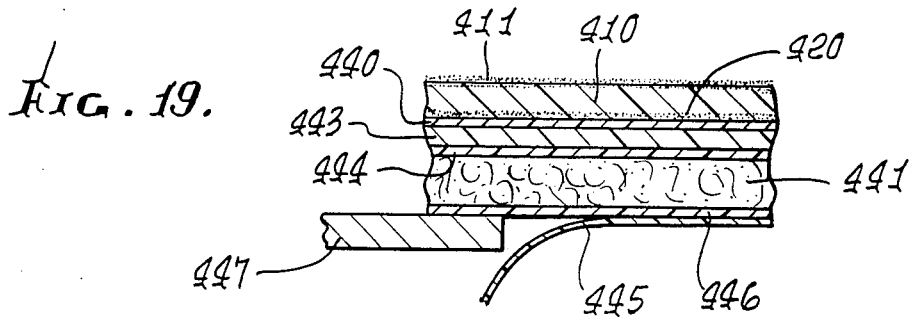

In the FIG. 19 composite, the numerals 410, 411, 420 also identify the same elements as in FIG. 15. In addition, other sheet means includes release liner 440 bonded to the first sheet, and auxiliary sheet structure carrying the liner. Such auxiliary sheet structure includes a foamed plastic layer 441, between about 1/16 and ¼ inches thick, for example, to provide cushioning (and corresponding to layer 423 in FIG. 16). In addition, the auxiliary sheet structure may include a carrier sheet 443 sandwiched between one side of the foamed layer 441 and the release liner 440, and carrying the latter. The sheet 443 is adhesively bonded at 444 to the foamed layer, and may comprise a polyester or Mylar sheet. A second release liner 445 is releasably adhesively bonded at 446 to the foamed layer, and may be peeled away to allow adhesive bonding to a carrier 447, as for example a file.

I claim:

1. A composite cosmetic device, comprising
   (a) a tough, flexible first sheet of silicone polymer, and having first and second sides,
   (b) abrasive particulate consisting of pumice carried by and protruding from the first side of the sheet and exposed for rubbing contact with human skin or other work, said sheet being stretchable, and being formed from a layer of initially incompletely cured silicone polymer with which said particulate has been combined to adhere to the sheet, the sheet then allowed to cure, and
   (c) other sheet means attached to said silicone polymer sheet and projecting from said second side thereof,
   (d) said particulate penetrating, and anchored by, the silicone polymer of the first sheet at said first side of the sheet,
   (e) said other sheet means including a release liner bonded to said first sheet, and auxiliary sheet structure carrying said release liner.

2. The composite of claim 1 wherein the first sheet thickness is between 0.015 and 0.100 inches.

3. The composite of claim 2 wherein the first sheet thickness is approximately uniform over the sheet area, and is between 0.020 and 0.060 inches.

4. The composite of claim 1 wherein said auxiliary sheet structure comprises a plastic sheet.

5. The composite of claim 1 wherein said auxiliary sheet structure includes a foamed plastic layer.

6. The composite of claim 5 wherein said auxiliary sheet structure includes a carrier sheet sandwiched between one side of said foamed layer and said release liner.

7. The composite of claim 5 further comprising a second release liner releasably bonded to said foamed layer.

8. The composite of claim 5 wherein said foam consists essentially of polyurethane and has exposed fibrous edges.

9. The composite of claim 5 wherein said foam is fibrous throughout, and has at least about 90% void space.

10. The composite of claim 5 wherein said foam is selected from the group consisting of polyethylene, polyurethane and polyvinylchloride.

* * * * *